United States Patent
Shin et al.

(10) Patent No.: US 9,629,605 B2
(45) Date of Patent: Apr. 25, 2017

(54) FORMATION OF A COLOR MAP FOR AN ELASTIC IMAGE

(75) Inventors: Dong Kuk Shin, Seoul (KR); Jong Sik Kim, Seoul (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 926 days.

(21) Appl. No.: 12/535,604

(22) Filed: Aug. 4, 2009

(65) Prior Publication Data
US 2010/0036250 A1   Feb. 11, 2010

(30) Foreign Application Priority Data
Aug. 5, 2008  (KR) ................. 10-2008-0076342

(51) Int. Cl.
*A61B 8/00* (2006.01)
*A61B 8/08* (2006.01)
(Continued)

(52) U.S. Cl.
CPC ............ *A61B 8/08* (2013.01); *A61B 8/14* (2013.01); *A61B 8/485* (2013.01); *G01S 7/52042* (2013.01); *G01S 7/52071* (2013.01)

(58) Field of Classification Search
CPC ........... A61B 8/00; A61B 8/463; A61B 8/485; A61B 8/0858; A61B 8/469; G01S 7/52042
(Continued)

(56) References Cited

U.S. PATENT DOCUMENTS 7,628,754 B2    12/2009  Matsumura et al.
2002/0186868 A1*  12/2002  Bjaerum et al. .............. 382/128
(Continued)

FOREIGN PATENT DOCUMENTS

EP    0772158 A2   5/1997
EP    1810620 A1   7/2007
(Continued)

OTHER PUBLICATIONS

Korean Office Action issued in Korean Patent Application No. 10-2008-0076342, mailed Jan. 4, 2011.
(Continued)

*Primary Examiner* — James Kish
(74) *Attorney, Agent, or Firm* — McDermott Will & Emery LLP

(57) ABSTRACT

Embodiments for forming a color map necessary for forming an elastic image in an ultrasound system. A transmission/reception (Tx/Rx) unit transmits ultrasound signals to a target object and receives ultrasound echo signals reflected from the target object to thereby obtain receive signals. The receive signals include first receive signals obtained before applying a stress to the target object and second receive signals obtained after applying a stress to the target object. An ultrasound data forming unit forms first and second ultrasound data based on the first and second receive signals, respectively. A processing unit computes strains by using the first and second ultrasound data and form a histogram based on the computed strains. The processing unit further clusters the histogram for separation into a plurality of clusters and forms a color map including a plurality of color map regions corresponding to the respective clusters.

12 Claims, 4 Drawing Sheets

(51) Int. Cl.
*A61B 8/14* (2006.01)
*G01S 7/52* (2006.01)

(58) Field of Classification Search
USPC ....... 600/407, 437, 438, 441, 442, 443, 445, 600/446, 458, 459, 463; 382/128, 164, 382/165, 170, 171, 172
See application file for complete search history.

(56) References Cited

U.S. PATENT DOCUMENTS

| | | | |
|---|---|---|---|
| 2003/0204142 A1* | 10/2003 | Brock-Fisher et al. | 600/458 |
| 2005/0065429 A1* | 3/2005 | Zhou | 600/412 |
| 2005/0227364 A1* | 10/2005 | Madsen et al. | 436/80 |
| 2006/0009700 A1* | 1/2006 | Brumfield et al. | 600/504 |
| 2006/0084125 A1* | 4/2006 | Laor | 435/7.23 |
| 2006/0084870 A1 | 4/2006 | Kim et al. | |
| 2006/0120608 A1 | 6/2006 | Luo et al. | |
| 2007/0038090 A1 | 2/2007 | Moon et al. | |
| 2007/0073145 A1* | 3/2007 | Fan et al. | 600/437 |
| 2007/0208263 A1* | 9/2007 | John et al. | 600/509 |
| 2007/0230653 A1 | 10/2007 | Okamoto et al. | |
| 2007/0242863 A1* | 10/2007 | Hoppel et al. | 382/128 |
| 2007/0263915 A1* | 11/2007 | Mashiach | 382/130 |
| 2008/0064956 A1 | 3/2008 | Jeong et al. | |
| 2009/0143676 A1* | 6/2009 | Matsumura | 600/438 |
| 2009/0216123 A1 | 8/2009 | Matsumura et al. | |

FOREIGN PATENT DOCUMENTS

| | | | |
|---|---|---|---|
| EP | 1938754 A1 | 7/2008 | |
| JP | 2003-102723 A | 4/2003 | |
| JP | 2004-261198 A | 9/2004 | |
| JP | 2006-110360 | 4/2006 | |
| JP | 2008-079770 A | 4/2008 | |
| JP | 2008-520345 A | 6/2008 | |
| JP | 2008-161674 A | 7/2008 | |
| KR | 10-2007-0013986 | 1/2007 | |
| KR | 10-2008-0024327 | 3/2008 | |
| WO | 2006/057304 A1 | 6/2006 | |
| WO | 2006/121031 A1 | 11/2006 | |
| WO | WO 2007046272 A1 * | 4/2007 | A61B 8/08 |

OTHER PUBLICATIONS

European Search Report for Application No. 09166289, mailed Nov. 6, 2009, 9 pages.

Arifin, et al., "Image segmentation by histogram thresholding using hierarchical cluster analysis," 27 Pattern Recognition Letters 1515, 1515-21 (2006).

Japanese Office Action, w/ English translation thereof, issued in Japanese Patent Application No. JP 2009-182325 dated Sep. 24, 2013.

\* cited by examiner

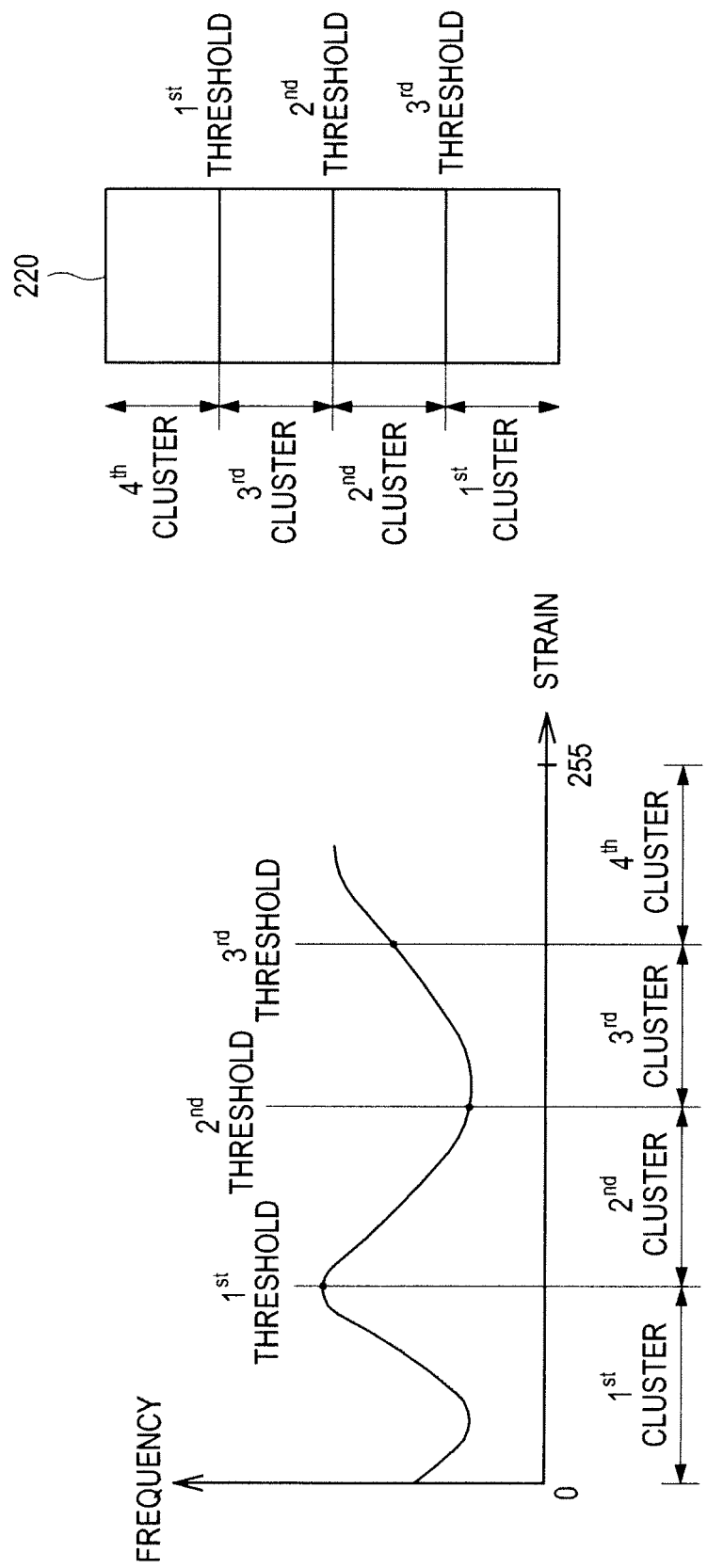

FORMATION OF A COLOR MAP FOR AN ELASTIC IMAGE

The present application claims priority from Korean Patent Application No. 10-2008-0076342 filed on Aug. 5, 2008, the entire subject matter of which is incorporated herein by reference.

TECHNICAL FIELD

The present disclosure generally relates to ultrasound systems, and more particularly to the formation of a color map for forming an elastic image in an ultrasound system.

BACKGROUND

An ultrasound system has become an important and popular diagnostic tool since it has a wide range of applications. Specifically, due to its non-invasive and non-destructive nature, the ultrasound system has been extensively used in the medical profession. Modern high-performance ultrasound systems and techniques are commonly used to produce two or three-dimensional images of internal features of an object (e.g., human organs).

Generally, the ultrasound image is displayed in a Brightness-mode (B-mode) by using reflectivity caused by an acoustic impedance difference between the tissues of the target object. However, if the reflectivity of the target object is hardly different from those of the neighboring tissues such as tumor, cancer or the like, then it is not easy to recognize the target object in the B-mode image.

To resolve the problem of recognizing the tumor, cancer and the like in the B-mode, an ultrasound elastic imaging technology has been developed to visualize mechanical characteristics of the tissues such as the elasticity thereof in the ultrasound system. Such technology is very helpful for diagnosing lesions such as tumor and cancer, which are hardly recognized in the B-mode image. The ultrasound elastic imaging technology may utilize the scientific property that the elasticity of the tissues is related to a pathological phenomenon. For example, the tumor or cancer is relatively stiffer than the neighboring normal tissues. Thus, when stress is uniformly applied, a displacement of the tumor or cancer is typically smaller than those of the neighboring tissues. In order to form an elastic image, strains representing deformation of the tissues due to the application of the stress should be measured. The strains may be measured by using two ultrasound data obtained before and after compressing the tissues.

Further, the ultrasound system may provide a color map, which maps strains to pseudo colors. The elastic image may be colored according to the color map so that the tissues in the elastic image may be distinguished from each other. The conventional ultrasound system may provide a color map, which is formed by previously set colors, regardless of a portion subject to examination that is formed as an elastic image. For example, the conventional color map may be formed to map relatively large strains to a red color and relatively small strains to a black color. Thus, when the target object may include bones, fats, soft tissues and cancer tissues, a relatively soft portion, such as fats and soft tissues, may be mapped to the red color and a relatively hard portion, such as bones and cancer tissues, may be mapped to the black color. Thus, it may be difficult to separate boundaries and positions between the tissues.

SUMMARY

Embodiments for forming a color map of an elastic image in an ultrasound system are disclosed herein. In one embodiment, by way of non-limiting example, an ultrasound system comprises: a transmission/reception (Tx/Rx) unit operable to transmit ultrasound signals to a target object and receive ultrasound echo signals reflected from the target object to thereby obtain receive signals, the receive signals including first receive signals obtained before applying a stress to the target object and second receive signals obtained after applying a stress to the target object; an ultrasound data forming unit operable to form first and second ultrasound data based on the first and second receive signals, respectively; and a processing unit operable to compute strains by using the first and second ultrasound data and form a histogram of the computed strains, the processing unit being further operable to cluster the histogram for separation into a plurality of clusters and form a color map including a plurality of color map regions corresponding to the respective clusters.

In another embodiment, a method of forming a color map for an elastic image in an ultrasound system, comprises: a) transmitting ultrasound signals to a target object and receiving ultrasound echo signals reflected from the target object to thereby obtain receive signals, the receive signals including first receive signals obtained before applying a stress to the target object and second receive signals obtained after applying a stress to the target object; b) forming first and second ultrasound data based on the first and second receive signals, respectively; c) computing strains by using the first and second ultrasound data; d) forming a histogram of the computed strains; e) clustering the histogram for separation into a plurality of clusters; and f) forming a color map including a plurality of color map regions corresponding to the respective clusters.

The Summary is provided to introduce a selection of concepts in a simplified form that are further described below in the Detailed Description. This Summary is not intended to identify key or essential features of the claimed subject matter, nor is it intended to be used in determining the scope of the claimed subject matter.

BRIEF DESCRIPTION OF THE DRAWINGS

FIGS. 4 and 5 are schematic diagrams showing examples of thresholds and clusters obtained through clustering and color maps formed based thereon.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Figure 1:
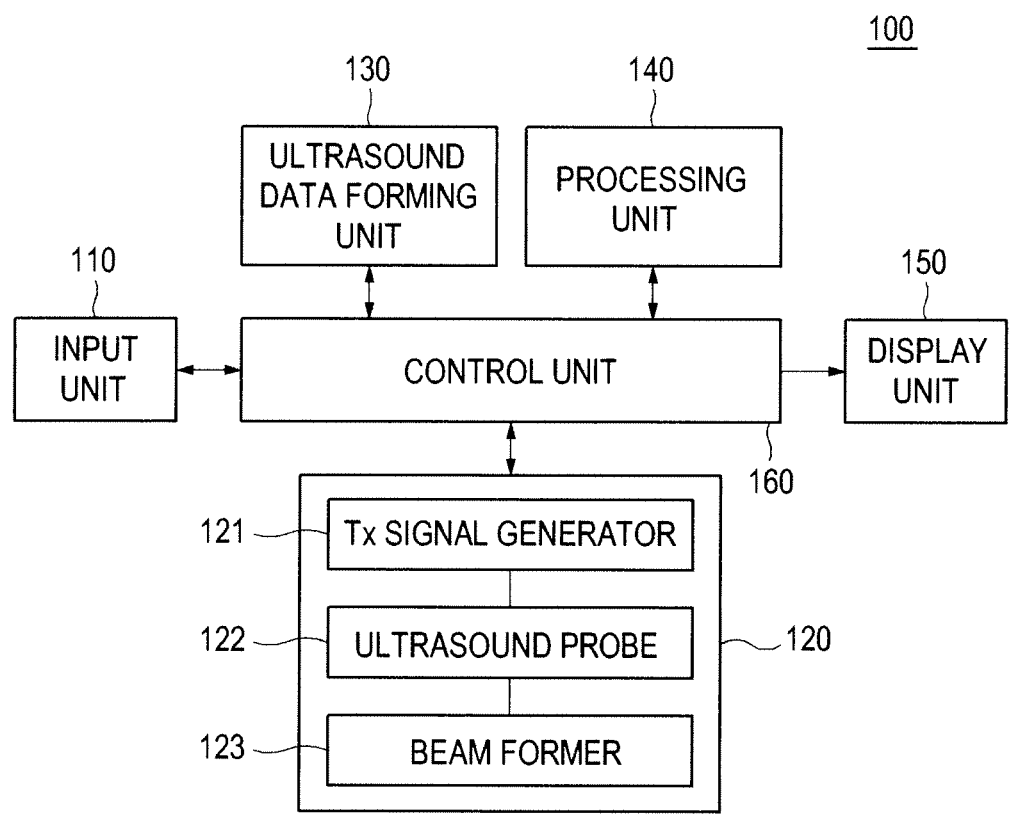
FIG. 1 is a block diagram showing an illustrative embodiment of an ultrasound system.

FIG. 1 is a block diagram showing an illustrative embodiment of an ultrasound system 100. Referring to FIG. 1, the ultrasound system 100 may include an input unit 110 that may be operable to receive user inputs. In one embodiment, the input unit 100 may include a control panel, a mouse and a keyboard. However, it is certainly not limited thereto.

The ultrasound system 100 may further include a transmission/reception (Tx/Rx) unit 120 that may be operable to transmit ultrasound signals to the target object and receive ultrasound echo signals reflected from the target object to thereby form receive signals. In one embodiment, the Tx/Rx unit 120 may include a transmission (Tx) pulse generator 121, an ultrasound probe 122 and a beam former 123.

The Tx pulse generator 121 may be operable to generate Tx pulses. In one embodiment, a Tx pattern of the Tx pulses may be formed for a B-mode image. The ultrasound probe 122 may include at least one transducer element for reciprocal conversion between electrical signals and ultrasound signals. The ultrasound probe 122 may be operable to receive the Tx pulses and transmit ultrasound signals into the target object in response thereto. The ultrasound probe 122 may be further operable to receive ultrasound echo signals reflected from the target object and convert them into electrical receive signals. The electrical receive signals may be analog signals. In one embodiment, a stress may be applied to the target object by using the probe. The probe may include a compression plate at a front side for compression. The electrical receive signals may include first receive signals obtained before applying a stress to the target object and second receive signals obtained after applying a stress to the target object.

The beam former 123 may be operable to convert the electrical receive signals into digital receive signals and apply delays to the digital receive signals in consideration of distances between the transducer elements and focal points. The beam former 123 may be further operable to sum the digital receive signals with the delays applied, thereby outputting receive-focused digital signals. The receive-focused digital signals may include first digital signals corresponding to the first receive signals and second digital signals corresponding to the second receive signals.

The ultrasound system 100 may further include an ultrasound data forming unit 130. The ultrasound data forming unit 130 may be embodied by a digital signal processor. The ultrasound data forming unit 130 may receive the first and second digital signals from the Tx/Rx unit 120 and perform signal processing thereupon such as gain adjustment, time gain compensation and the like, thereby forming ultrasound data. In one embodiment, the ultrasound data forming unit 130 may be operable to form first ultrasound data corresponding to a first frame based on the first digital signals. Also, the ultrasound data forming unit 130 may be further operable to form second ultrasound data corresponding to a second frame based on the second digital signals.

The ultrasound system 100 may further include a processing unit 140. The processing unit 140 may be operable to compute strains by comparing the first and second ultrasound data. The processing unit 140 may be further operable to form a color map based on the computed strains. The processing unit 140 may be further operable to form an elastic image based on the computed strains and the color map.

The ultrasound system 100 may further include a display unit 150. The display unit 150 may display the color map formed in the processing unit 140. Also, the display unit 150 may further display the elastic image formed in the elastic image forming section 147 of the processing unit 140.

The ultrasound system 100 may further include a control unit 160 that may be operable to control the display unit 150 to display the elastic image and the color map. Also, the control unit 160 may be operable to control entire operations of the ultrasound system 100.

Figure 2:
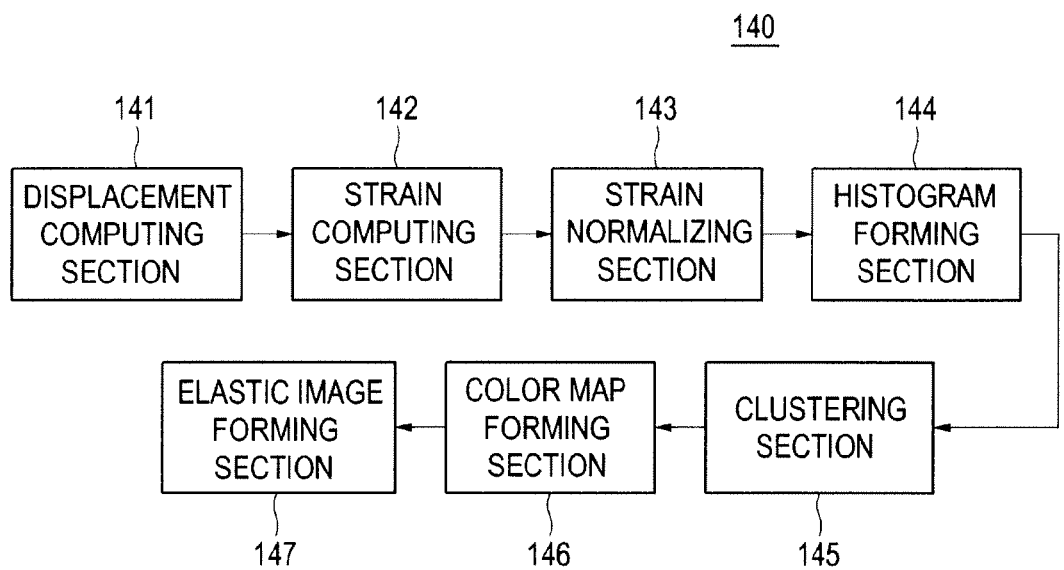
FIG. 2 is a block diagram showing an illustrative embodiment of the processing unit shown in FIG. 1.

FIG. 2 is a block diagram showing an illustrative embodiment of the processing unit 140. Referring to FIG. 2, the processing unit 140 may include a displacement computing section 141. The displacement computing section 141 may be operable to compute displacements in a pixel unit between first and second frames. Also, the displacement computing section 141 may be operable to compute displacement in a block unit (e.g., 4×4, 8×8, etc.). In one embodiment, the displacements may be computed by using cross-correlation or auto-correlation. However, the computation of the displacements may not be limited thereto.

The processing unit 140 may further include a strain computing section 142. The strain computing section 142 may be operable to compute local strains based on the displacement computed in a pixel unit or a block unit. The strains may be computed by one of the well-known strain computation methods. Thus, the detailed descriptions thereof will be omitted herein.

The processing unit 140 may further include a strain normalizing section 143. The strain normalizing section 143 may be operable to normalize the computed strains. In one embodiment, the strain normalizing section 143 may be operable to detect maximum and minimum strains from the computed strains, and map the strains to values ranging from 0 to 255. In such a case, the minimum strain may be mapped to 0 and the maximum strain may be mapped to 255.

In one embodiment, the strain normalizing section 143 may be operable to compute a mean and standard deviation of the strains. The strain normalizing section 143 may be further operable to subtract standard deviation multiplied by 2 from the mean, i.e., perform an operation of (mean−2× standard deviation), and set the operation result as a minimum value. The strain normalizing section 143 may be further operable to add standard deviation multiplied by 2 to the mean, i.e., perform an operation of (mean+2×standard deviation), and set the operation result as a maximum value. The strain normalizing section 143 may be operable to map the strains to values ranging from 0 to 255. In such a case, the strains, which are equal to or greater than the maximum value, may be mapped to 255. Further, the strains, which are equal to or less than the minimum value, may be mapped to 0.

Figure 3:
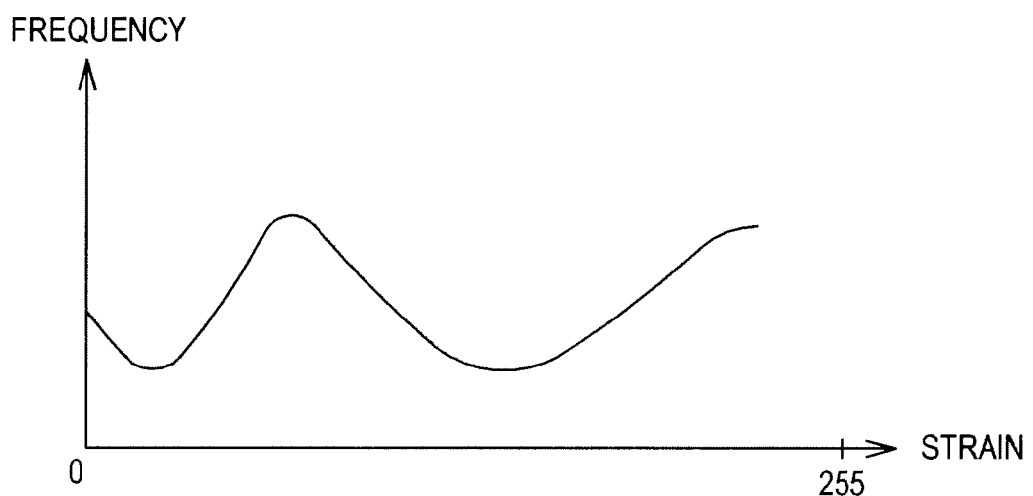
FIG. 3 is a schematic diagram showing an illustrative embodiment of a histogram of normalized strains.

The processing unit 140 may further include a histogram forming section 144. The histogram forming section 144 may be operable to form a histogram based on the normalized strains. In the histogram, a horizontal axis may represent a strain and a vertical axis may represent a frequency, as shown in FIG. 3.

The processing unit 140 may further include a clustering section 145. The clustering section 145 may be operable to cluster the histogram for separation into a plurality of clusters. The number of clusters may be selected according to the type of the target object. For example, if the target object may include fats, soft tissues, muscles and bones, then a four number of the clusters may be selected.

Figure 4:
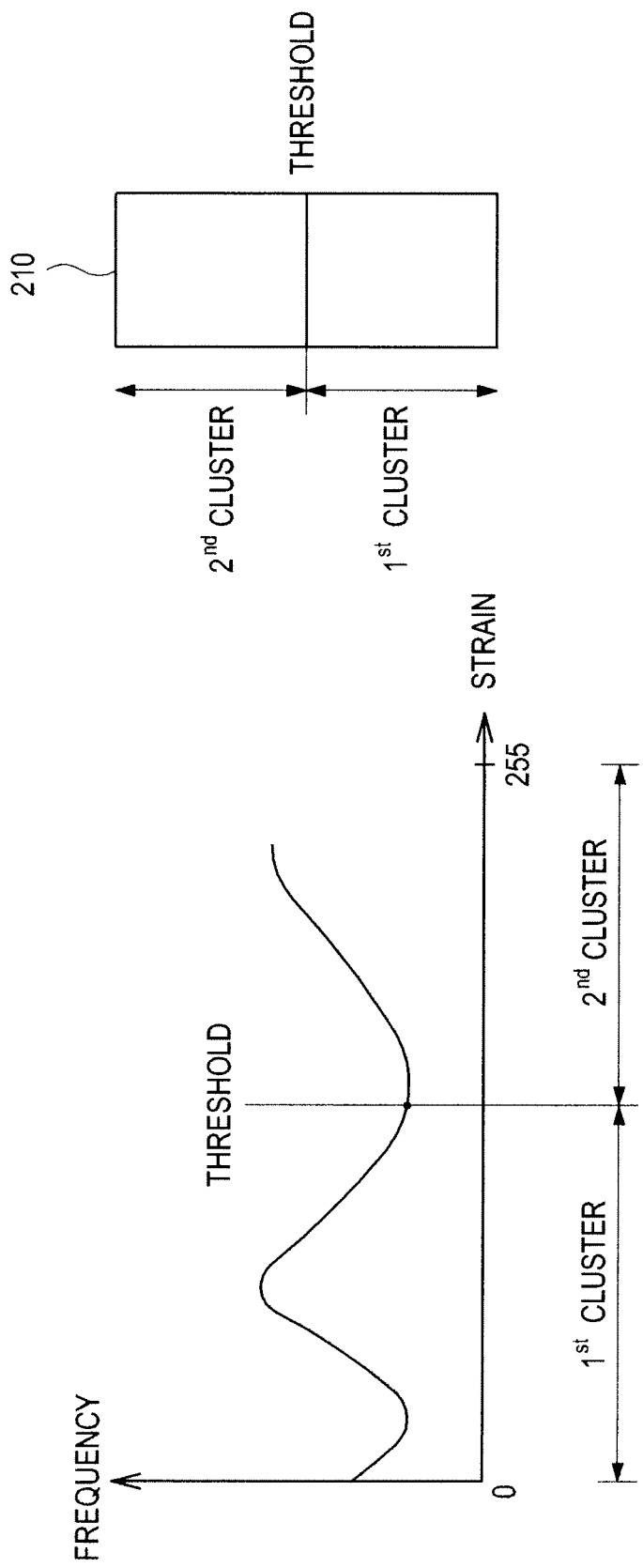

In one embodiment, the clustering may be performed by using the Otsu algorithm. If a user input for selecting the number of the clusters (e.g., 2) is inputted through the input unit 110, then the clustering section 145 may be operable to find a threshold by clustering the histogram using the Otsu algorithm. The clustering section 145 may be further operable to separate the histogram into two regions, i.e., a first cluster and a second cluster with reference to the threshold, as illustrated in FIG. 4. Further, if a user input for determining the number of the clusters (e.g., 4) is inputted through the input unit 110, then the clustering section 145 may be operable to find three thresholds by clustering the histogram using the Otsu algorithm twice. The clustering section 145 may be further operable to separate the histogram into four regions, i.e., a first cluster, a second cluster, a third cluster and a fourth cluster with reference to the three thresholds, as illustrated in FIG. 5. In another embodiment, the thresholds may be found by using the k-means clustering algorithm.

Although it is described above that the Otsu algorithm and the k-means clustering algorithm may be adopted to cluster the histogram, the algorithms for clustering are certainly not limited thereto. Any algorithms capable of performing the clustering may be adopted.

The processing unit 140 may further include a color map forming section 146. The color map forming section 146 may be operable to form a color map 210 that maps the strains to colors, as shown in FIG. 4. In one embodiment, the color map 210 may be divided into a plurality of color map regions according to the threshold found by the clustering section 145. That is, the number of color map regions may be determined to be equal to the number of clusters. In one embodiment, colors at each of the color map regions may be independently mapped to the strains. For example, when there are first and second clusters, the color map 210 may be divided into a first color map region and a second color map region. In such a case, the color mapping in the first color map region may be carried out based on the strains included in the first cluster, while the color mapping in the second color map region may be carried out based on the strains included in the second cluster. Also, when there are four clusters, the color map forming section 146 may be operable to form a color map consisting of four color map regions, as shown in FIG. 5.

Although it is described above that the colors are differently mapped at each of the color map regions, the color mapping is certainly not limited thereto. In another embodiment, an identical color may be mapped to the color map regions, and brightness thereof may be differently adjusted for each of the color map regions. Also, the color at each of the color map regions may be mapped such that a region close to the threshold becomes dark and a region far to the threshold becomes light.

The processing unit 140 may further comprise an elastic image forming section 147. In one embodiment, the elastic image forming section 147 may be operable to form an elastic image of the target object based on the strains computed by the strain computing section 142 and the color map formed by the color map forming section 146. Also, the elastic image forming section 147 may be operable to form an elastic image of the target object based on the strains normalized in the strain normalizing section 143.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system, comprising:
   a probe configured to transmit ultrasound signals to a target object and receive ultrasound echo signals reflected from the target object to thereby obtain first and second receive signals, the first receive signal being obtained before applying a stress to the target object and the second receive signal being obtained after applying a stress to the target object;
   a processor configured to compute strains by using first ultrasound data formed based on the first receive signal and second ultrasound data formed based on the second receive signal and configured to form a histogram of the computed strains;
   a user interface, coupled to the processor, configured to receive a user input for selecting a number n which is an integer equal to or greater than 2, the number n indicating into how many histogram clusters the histogram is to be divided, the number n being selected according to a type of the target object; and
   a display coupled to the processor,
   wherein the processor is further configured to compute mean and standard deviation of the computed strains and a maximum value as a result of an operation of (mean−2×standard deviation) and a minimum value as a result of an operation of (mean+2×standard deviation),
   wherein the processor is further configured to normalize the computed strains by mapping the strains to values ranging from 0 to 255, the strains equal to or lower than the minimum value being mapped to 0 and the strains equal to or higher than the maximum value being mapped to 255,
   wherein the processor automatically determines n−1 threshold values between 0 and 255 which separate the histogram into n histogram clusters by using an Otsu algorithm less than n times, the n−1 threshold strain values including a first threshold strain value, the n histogram clusters including a first histogram cluster of the histogram of the computed strains between a first lower limit of strain value and a first upper limit of strain value that are below the first threshold strain value, and a second histogram cluster of the histogram of the computed strains between a second lower limit of strain value and a second upper limit of strain value that are above the first threshold strain value,
   forms a color map for strain-to-color mapping of the strains, the color map including n color map regions respectively corresponding to the n histogram clusters including the first histogram cluster and the second histogram cluster, wherein the number of the plurality of color map regions equals to the number of the plurality of histogram clusters, and
   independently maps colors at each of the color map regions to the strains,
   wherein the display is configured to display the color map.

2. The ultrasound system of claim 1, wherein the processor is further configured to compute:
   displacements by comparing the first and second ultrasound data; and
   the strains based on the computed displacements.

3. The ultrasound system of claim 2, wherein the color map regions are mapped to different colors.

4. The ultrasound system of claim 2, wherein the color map regions are mapped to a color having different brightness from each other.

5. The ultrasound system of claim 2, wherein the processor is further configured to normalize:
   computing mean and standard deviation of the computed strains;
   performing an operation of (mean−2×standard deviation) to set the operation result as the minimum strain; and
   performing an operation of (mean+2×standard deviation) to set the operation result as the maximum strain.

6. The ultrasound system of claim 1, wherein each of the n histogram clusters includes a set of strain values and frequency values.

7. A method of forming a color map for an elastic image in an ultrasound system comprising a processor, a probe, a user interface, a display which executes the method, the method comprising:
- transmitting, by the probe, ultrasound signals to a target object and receiving ultrasound echo signals reflected from the target object to thereby obtain first receive signal, the first receive signal being obtained before applying a stress to the target object;
- applying stress to the target object;
- transmitting, by the probe, ultrasound signals to a target object and receiving ultrasound echo signals reflected from the target to thereby obtain second receive signals, the second receive signal being obtained after applying the stress to the target object;
- computing, by the processor, strains by using first ultrasound data formed based on the first receive signal and second ultrasound data formed based on the second receive signal;
- forming, by the processor, a histogram of the computed strains;
- receiving, by the user interface, a user input for selecting a number n which is an integer equal to or greater than 2, the number n indicating into how many histogram clusters the histogram is to be divided, the number n being selected according to a type of the target object;
- computing, by the processor, mean and standard deviation of the computed strains and a maximum value as a result of an operation of (mean−2×standard deviation) and a minimum value as a result of an operation of (mean+2×standard deviation),
- normalizing, by the processor, the computed strains by mapping the strains to values ranging from 0 to 255, the strains equal to or lower than the minimum value being mapped to 0 and the strains equal to or higher than the maximum value being mapped to 255;
- automatically determining, by the processor, n−1 threshold values between 0 and 255 which separate the histogram into n histogram clusters by using an Otsu algorithm less than n times, the n−1 threshold strain values including a first threshold strain value, the n histogram clusters including a first histogram cluster of the histogram of the computed strains between a first lower limit of strain value and a first upper limit of strain value that are below the first threshold strain value, and a second histogram cluster of the histogram of the computed strains between a second lower limit of strain value and a second upper limit of strain value that are above the first threshold strain value; and
- forming, by the processor, a color map for strain-to-color mapping of the strains, the color map including n color map regions respectively corresponding to the n histogram clusters including the first histogram cluster and the second histogram cluster, and mapping colors at each of the color map regions to the strains independently, wherein the number of the plurality of color map regions equals to the number of the plurality of histogram clusters,
- displaying, by the display, the color map.

8. The method of claim 7, wherein the computing of strains includes:
- computing displacements by comparing the first and second ultrasound data; and
- computing the strains based on the computed displacements.

9. The method of claim 8, wherein the color map regions are mapped to different colors.

10. The method of claim 8, wherein the color map regions are mapped to a color having different brightness from each other.

11. The method of claim 8, wherein the normalizing of the strains includes:
- computing mean and standard deviation of the strains;
- performing an operation of (mean−2×standard deviation) to set the operation result as the minimum strain; and
- performing an operation of (mean+2×standard deviation) to set the operation result as the maximum strain.

12. The method of claim 7, wherein each of the n histogram clusters includes a set of strain values and frequency values.

* * * * *